US011612470B2

(12) United States Patent
Kumar

(10) Patent No.: US 11,612,470 B2
(45) Date of Patent: Mar. 28, 2023

(54) SWINE VACCINATION SYSTEM

(71) Applicant: Zoetis Services LLC, Parsippany, NJ (US)

(72) Inventor: Mahesh Kumar, Portage, MI (US)

(73) Assignee: Zoetis Services LLC, Parsippany, NJ (US)

( * ) Notice: Subject to any disclaimer, the term of this patent is extended or adjusted under 35 U.S.C. 154(b) by 218 days.

(21) Appl. No.: 15/279,506

(22) Filed: Sep. 29, 2016

(65) Prior Publication Data

US 2017/0014213 A1 Jan. 19, 2017

Related U.S. Application Data

(60) Continuation of application No. 14/296,590, filed on Jun. 5, 2014, now abandoned, which is a division of
(Continued)

(51) Int. Cl.
*A61D 1/02* (2006.01)
*A61M 11/00* (2006.01)
(Continued)

(52) U.S. Cl.
CPC ............. *A61D 1/025* (2013.01); *A61D 7/04* (2013.01); *A61M 11/00* (2013.01);
(Continued)

(58) Field of Classification Search
CPC .... A61D 1/025; A61D 7/04; A61D 2003/003; A61M 11/00; A61M 2205/13;
(Continued)

(56) References Cited

U.S. PATENT DOCUMENTS 870,766 A 11/1907 Eaton
883,132 A 3/1908 Goff
(Continued)

FOREIGN PATENT DOCUMENTS

AU 500020 B2 5/1979
CA 2416726 A1 7/2004
(Continued)

OTHER PUBLICATIONS

International Search Report PCT/US2009/032363, dated Feb. 25, 2010.
(Continued)

*Primary Examiner* — Magdalena Topolski
(74) *Attorney, Agent, or Firm* — Womble Bond Dickinson (US) LLP

(57) ABSTRACT

A system for vaccinating swine according to one embodiment includes a housing having an open first end and an open opposite second end. The housing has a pair of side walls that are angled and non-parallel to one another such that at the second end only a single piglet can exit at one time. The system also includes a vaccination station for individually vaccinating piglets. The vaccination station is located between the pair of side walls in a region thereof that is sized to only permit one piglet to stand between the side walls. The vaccination station includes at least one sensor that detects the presence of the one piglet within the vaccination station and at least one spray nozzle positioned within the vaccination station such that a vaccine dose discharged therefrom is directed upwardly into facial areas of the piglet effectively.

9 Claims, 7 Drawing Sheets

Related U.S. Application Data application No. 12/864,130, filed as application No. PCT/US2009/032363 on Jan. 29, 2009, now abandoned.

(60) Provisional application No. 61/025,202, filed on Jan. 31, 2008.

(51) Int. Cl.
*A61D 7/04* (2006.01)
*A61D 3/00* (2006.01)

(52) U.S. Cl.
CPC ... *A61D 2003/003* (2013.01); *A61M 2205/13* (2013.01); *A61M 2205/3379* (2013.01); *A61M 2210/0606* (2013.01); *A61M 2250/00* (2013.01)

(58) Field of Classification Search
CPC .. A61M 2205/3379; A61M 2210/0606; A61M 2250/00; A01K 13/003
USPC ....... 119/712, 732, 737, 751, 752, 843, 845, 119/757; 452/54
See application file for complete search history.

(56) References Cited

U.S. PATENT DOCUMENTS

| | | | |
|---|---|---|---|
| 2,526,037 A | 10/1950 | Murphy | |
| 3,138,141 A | 6/1964 | Poage | |
| 3,464,392 A | 9/1969 | Hoyme et al. | |
| 3,699,928 A * | 10/1972 | Cowan | A01K 13/003 119/667 |
| 3,970,045 A | 7/1976 | Graham, Jr. | |
| 4,263,909 A * | 4/1981 | Bush | A61M 5/00 222/372 |
| 4,449,968 A | 5/1984 | Peterson | |
| 4,459,942 A * | 7/1984 | Cauthron | A01K 13/003 119/666 |
| 4,535,726 A * | 8/1985 | Cauthron | A01K 13/003 119/666 |
| 4,674,490 A | 6/1987 | Frankel et al. | |
| 4,781,150 A | 11/1988 | Phillips | |
| 4,850,997 A * | 7/1989 | DuBose | A61D 1/025 604/289 |
| 4,987,861 A * | 1/1991 | Lemire | A01K 13/001 119/667 |
| 5,027,747 A * | 7/1991 | Talley | A01K 13/003 119/652 |
| 5,056,467 A | 10/1991 | Schaefer | |
| 5,063,880 A * | 11/1991 | Bouthillier | A01K 13/001 119/667 |
| 5,070,818 A | 12/1991 | Gearn et al. | |
| 5,297,502 A | 3/1994 | Jaeger | |
| 5,630,379 A | 5/1997 | Gerk et al. | |
| 5,738,045 A | 4/1998 | Bleacher | |
| 5,758,603 A * | 6/1998 | Vivier | A01K 13/003 119/669 |
| 5,950,562 A | 9/1999 | Schulte et al. | |
| 6,021,742 A | 2/2000 | Cummings | |
| 6,029,610 A * | 2/2000 | Ramsey | A01K 13/001 119/651 |
| 6,085,697 A | 7/2000 | Fuchs | |
| 6,443,164 B1 * | 9/2002 | Parker | A61M 35/00 132/333 |
| 6,520,118 B2 * | 2/2003 | Swiegers | A01K 13/003 119/666 |
| 6,615,769 B2 * | 9/2003 | Zhioua | A01K 13/003 119/657 |
| 6,651,587 B1 | 11/2003 | DeFord et al. | |
| 6,651,589 B2 | 11/2003 | Greeson | |
| 6,910,446 B2 * | 6/2005 | Johnston Jr. | A01K 45/00 119/651 |
| 7,104,220 B1 | 9/2006 | Mack et al. | |
| 7,140,325 B2 * | 11/2006 | Lowe | A01K 13/003 239/550 |
| 7,851,605 B2 * | 12/2010 | Kwon | A61K 39/102 536/23.1 |
| 9,339,009 B1 * | 5/2016 | Larson | A01K 13/003 |
| 2002/0104485 A1 * | 8/2002 | Lewis | A61D 1/025 119/72.5 |
| 2005/0224596 A1 * | 10/2005 | Panopoulos | A01M 1/2038 239/67 |
| 2007/0006814 A1 | 1/2007 | Mead et al. | |
| 2008/0171066 A1 * | 7/2008 | Cutting | A61K 39/00 424/246.1 |
| 2010/0059608 A1 * | 3/2010 | Obata | A45D 44/00 239/690 |

FOREIGN PATENT DOCUMENTS

| | | | |
|---|---|---|---|
| CH | 696184 | 2/2007 | |
| FR | 2879094 | 6/2006 | |
| JP | H01124451 | 5/1989 | |
| JP | H02114027 | 9/1990 | |
| JP | H03-21313 | 1/1991 | |
| JP | H06-237662 | 8/1994 | |
| JP | 2001-161200 | 6/2001 | |
| JP | 2007-195869 | 8/2007 | |
| WO | WO 01/91563 A2 | 12/2001 | |
| WO | WO 02/36041 A1 | 5/2002 | |
| WO | WO 03/003820 A1 | 1/2003 | |
| WO | WO 2007/135248 | 11/2007 | |
| WO | WO-2012016328 A1 * | 2/2012 | A61D 1/025 |
| WO | WO-2018037417 A1 * | 3/2018 | |
| WO | WO-2020018325 A1 * | 1/2020 | A61D 1/025 |

OTHER PUBLICATIONS

PCT Written Opinion PCT/US2009/032363.
Japanese Office Action, Japanese Patent Application No. 2010-545140, translation in English.

\* cited by examiner

SWINE VACCINATION SYSTEM

CROSS REFERENCE TO RELATED APPLICATIONS

This application is a continuation of U.S. application Ser. No. 14/296,590, filed Jun. 5, 2014, which was a divisional of U.S. application Ser. No. 12/864,130, filed Jul. 22, 2010, which was the National Stage of International Application No. PCT/US09/32363, filed Jan. 29, 2009, which claims the benefit of U.S. Provisional Application No. 61/025,202, filed Jan. 31, 2008, all of which are expressly incorporated herein by reference in their entirety.

BACKGROUND

Swine, when raised commercially, typically are vaccinated to prevent infectious diseases which otherwise could rapidly propagate to infect all swine housed together. Swine producers should vaccinate their pigs to prevent or decrease economic loss from important infectious diseases. Infectious diseases are caused by microorganisms, such as bacteria or viruses. As is known, vaccines contain "safe" microorganisms which are injected into a pig to prepare its immune system to resist diseases. Swine should be vaccinated for a disease before they will encounter the microorganisms causing it.

Leptospirosis (lepto) is a disease which can cause abortion. Sows and gilts should be vaccinated against Leptospirosis bacteria before breeding. Many lepto vaccines call for gilts to be vaccinated twice before breeding, while sows should receive a single booster vaccination at every weaning.

For some piglet diseases, such as scours caused by *E. coli* bacteria, often the best strategy is to vaccinate the sow before farrowing. The vaccination increases the concentration of antibodies in the sow's colostrums, or first milk produced after farrowing. These antibodies are absorbed into the piglets' bodies, providing temporary protection until their immune systems are able to provide their own.

Swine are routinely vaccinated for: (1) Atrophic rhinitis (*Pasteurella multocida* type A and toxigenic type D and *Bordetella bronchiseptica*) —infection with these organisms can cause deviation of the snout and increases respiratory disease on some farms. Females are vaccinated before farrowing so they will pass on protection to their piglets in the colostrums (first milk after farrowing); (2) *E. Coli*—infection of baby pigs with types of this bacteria from fecal contamination of the environment can cause severe scours; (3) Erysipelas (*Erysipelothrix rhusiopathiae*) —infection with this bacterium can spread throughout the body of growing pigs. It can cause death or can localize in the joints, causing chronic arthritis or heart infections; and (4) Leptospirosis—infection of susceptible pregnant females with the *Leptospira* bacterium can result in abortion. There are a number of other diseases that can be the subject of a vaccination, e.g., H1N1 influenza virus is referred to as traditional swine flu and the H3N2 influenza virus is referred to as new swine flu. Other diseases include Porcine Circovirus (PCV) which can lead to postweaning multisystemic wasting syndrome (PMWS) which over time results in significant depletion of lymphocytes, the PRRS virus (porcine reproductive and respiratory syndrome virus), a.k.a. the Mystery Swine Disease Syndrome, which causes abortions, stillbirths, mummies, and weakborn piglets, and *Mycoplasma hyopneumoniae* which produces a chronic bronchopneumonia. Vaccination of swine on a commercial scale is typically accomplished by injection where each pig is individually injected with vaccine. There are several injection types and placements. More specifically, the injection can be a subcutaneous injection where the injection is under the skin (e.g., loose flaps of skin in the flank and elbow or behind the ears). The injection can be an intramuscular injection where the injection is into the muscle (e.g., spot on the neck just behind and below the ear). The injection can be an intraperitoneal injection where the injection is in the abdominal cavity. The injection can be an intravenous injection in the vein. The injection can be an intranasal injection in the nasal passages. In all these vaccination procedures, a needle of appropriate size is used and the pig is injected is an appropriate place.

While, spray vaccinator systems have been developed for the poultry industry, these systems are specifically tailored for this industry and are not suitable for use with swine. More specifically, in spray vaccinator systems, the chicks are sprayed with a solution containing the desired vaccination. The spray enters the body or each chick through its mucous membrane, typically at the eyes or nostrils of the chick, and thereby accomplishes the desired vaccination. Additionally, the nature of preening (running their beaks through their feathers or scratching their heads with a toe) allows uptake of vaccine that is deposited over the feathers of the chick and is considered a part of the vaccination process. This also results in the spray entering the mucous membrane of the chick. Examples of poultry vaccination systems are disclosed in U.S. Pat. Nos. 4,449,968 and 4,850,997. However, in all these systems, a cabinet or tray or the like is provided for receiving and holding a number of chicks (e.g., 100 chicks). The spray mechanism typically includes a shower device that is located above the cabinet and sprays the vaccine downwardly into the open top and onto the chicks. The droplets thus land on the upper body portions of the chicks. While these systems are suitable for use with a large number of small chicks that can be placed into the floor of the cabinet, this arrangement is not suitable for swine which has a much larger size and is also more mobile. In addition, unlike chicks, swine do not preen themselves and thus, a more precise and direct delivery of the vaccination into the mucous membrane is needed.

There is thus a need for a spray vaccination system that is specifically designed for use with swine.

SUMMARY

A system for vaccinating swine according to one embodiment includes a housing having an open first end and an open opposite second end. The housing has a pair of side walls that are angled and nonparallel to one another such that at the second end only a single piglet can exit at one time.

The system also includes a vaccination station for individually vaccinating piglets. The vaccination station is located between the pair of side walls in a region thereof that is sized to only permit one piglet to stand between the side walls. The vaccination station includes at least one sensor that detects the presence of the one piglet within the vaccination station and at least one spray nozzle positioned within the vaccination station such that a vaccine dose discharged therefrom is directed upwardly into facial areas of the piglet effectively.

In another embodiment, a system for vaccinating swine includes a housing having an open first end that serves as an entrance and an open opposite second end that serves as an exit. The housing is defined by a wall that tapers inwardly toward the second end. The housing is angled relative to a ground plane such that the second end is positioned lower than the first end to cause the housing to slope downward from the first end to the second end.

The system also includes a vaccination station for individually vaccinating piglets. The vaccination station is located within the housing between the first and second ends. The vaccination station includes at least one sensor that detects the presence of the one piglet within the vaccination station and at least one spray nozzle positioned within the vaccination station such that a vaccine dose discharged therefrom is directed upwardly into facial areas of the piglet effectively.

As used throughout, the term spray nozzle is used to define either a single discharge orifice or multiple discharge orifices grouped into one fixture, e.g. a "spout" or a "shower head" type design. Further, the vaccine dose discharged through the spray nozzle can be in liquid, aerosol, or gas form. Furthermore, the spray pattern from the nozzle can vary from a single stream to a pattern of multiple divergent streams to a mist.

BRIEF DESCRIPTION OF THE DRAWING FIGURES

DETAILED DESCRIPTION

Figure 1:
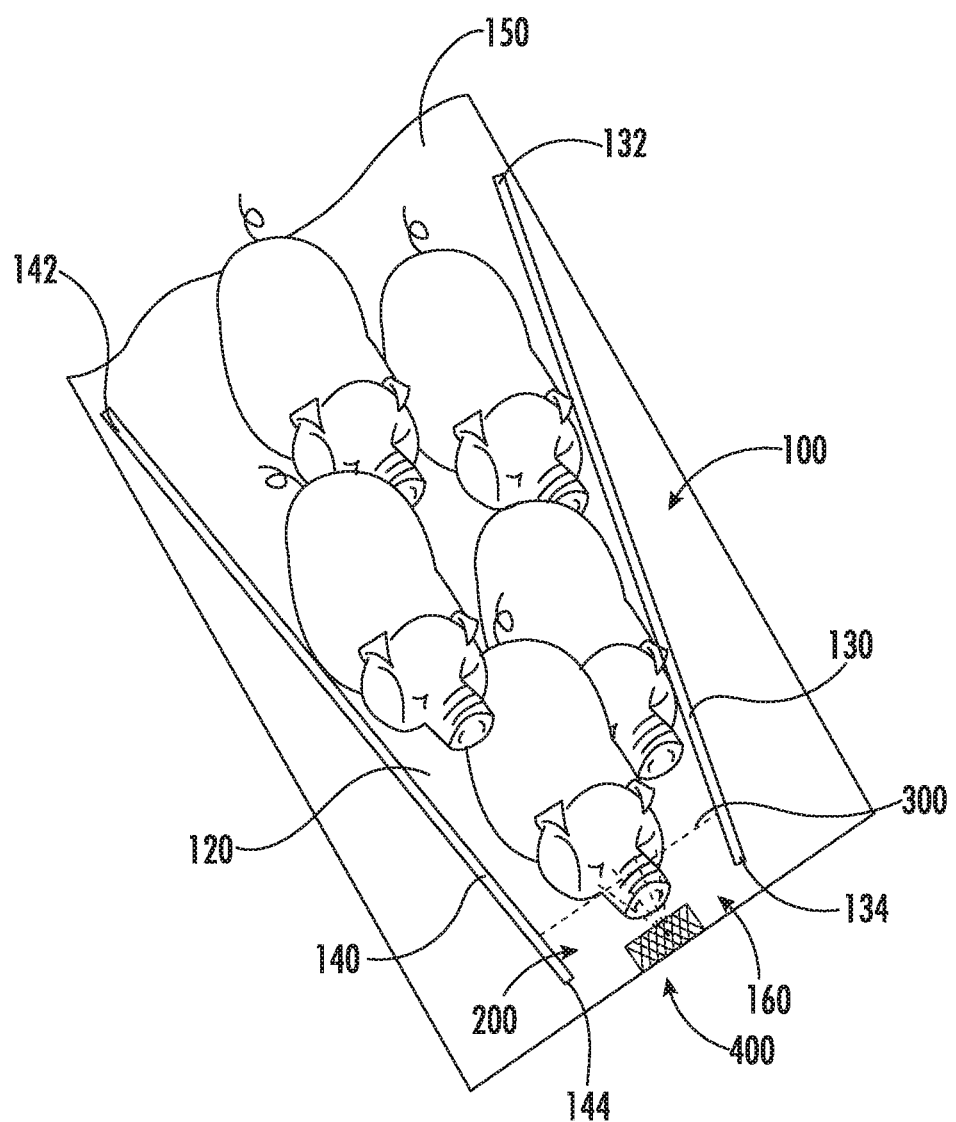
FIG. 1 is a top plan view of a swine spray vaccination system according to one embodiment.
Figure 2:
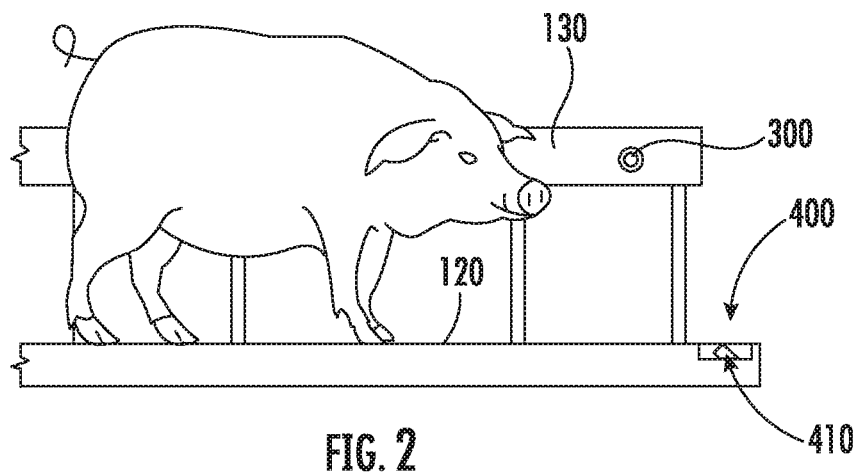
FIG. 2 is a side elevation view of the swine spray vaccination system of FIG. 1.
Figure 5:
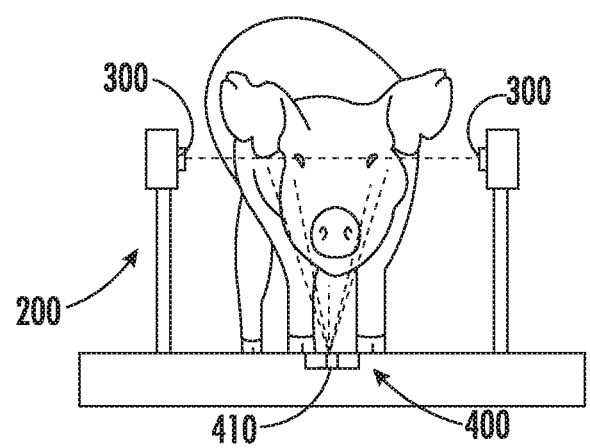
FIG. 5 is an end elevation view of the swine spray vaccination system of FIG. 1.

Referring first to FIGS. 1, 2 and 5 which illustrate a swine spray vaccination system 100 according to one embodiment. The system 100 can include a housing 110 that is formed of a floor 120, a first side wall 130 and a second side wall 140. The first and second side walls 130, 140 are upstanding walls that are spaced apart from one another. The side walls 130, 140 are not parallel to one another but instead are angled with respect to one another. As shown, the side walls 130, 140 are angled inwardly toward one another such that first ends 132, 142 of the side walls 130, 140 are spaced further apart from second ends 134, 144 of the side walls 130, 140. As shown in the top view of FIG. 1, the side walls 130, 140 are arranged generally in a "V" shape.

The housing 110 has a first end or an entrance 150 through which a number of piglets enter the housing between the side walls 130, 140, where the side walls 130, 140 are maximally spaced apart from one another. At an opposite end of the housing 110, a second end or exit 160 is provided through which each piglet exits the housing 110.

It will be appreciated that the housing 110 can be in the form of a box or tunnel structure and contains a narrowing chute that directs the piglets toward the exit 160 so as to allow for the vaccination of individual piglets. In particular, a group of piglets are directed into the entrance 150 of the housing 110 onto the floor 120 between the side walls 130, 140. The narrowing chute construction of the housing 110 causes a metering effect of the piglets since as the piglets move toward the exit 160, the tapering of the side walls 130, 140 causes only a single piglet to advance toward and into a vaccination station or region 200 where the piglets are vaccinated in an individual manner. In other words, the width between the walls 130, 140 in a region just before the vaccination station 200, within the vaccination station 200, and from the vaccination station 200 to the exit 160 only accommodates one piglet.

The use of system 100 is ideal during weaning of piglets from sows and prior to placement in finishing areas. The herding of piglets toward the housing 110 and then into the entrance 150 and along the floor 120 to the station 200 and finally the exit 160 allows individual vaccination of the piglet. The vaccination station 200 is thus located proximate to the exit 160 but in any event it is located where only a single piglet can be disposed between the two side walls 130, 140.

The vaccination station 200 includes one or more sensors 300 for detecting the presence of the piglet in the station 200. The sensor or sensors 300 can be any number of different types of sensors so long as they are cable of detecting the presence of the piglet in the station 200. For example, the sensor 300 can be of the type that detects the weight of the piglet and based on a detected difference in weight in a target area (sensor location), the sensor 300 sends a signal to a master controller indicating the presence of the piglet. The sensor 300 can also be of the type that detects movement of the piglet in the target area (sensor location) and then sends a signal to the master controller. The control signal is used to time the application of the vaccination to the piglet in the vaccination station 200.

The sensor 300 can be in the form of an optical sensor which detects the piglet when the piglet breaks the beam of the optical sensor as the piglet enters the vaccination station 200.

The vaccination station 200 also includes a means 400 for individually applying the vaccine to the piglet. According to the present invention, the application means 400 is in the form of a device that is capable of spraying the vaccine so as to administer the vaccine to the piglet. The spray means 400 is configured and located so that the vaccine is applied as a fine or course spray, as warranted by the vaccinating agent, which is delivered to the facial area of the piglet. For example and according to one embodiment, the spray means 400 is in the form of at least one and preferably a plurality of nozzle devices which spray the vaccine onto the piglet.

The spray nozzle 400 is located within housing 110 so as to deliver the vaccination to the facial area of the piglet. Thus, and in complete contrast to a traditional poultry spray system, the spray nozzle 400 or nozzles 400 are located not above the housing 110 but are below the piglet such that the vaccine is directed upwardly into the face of the piglet. For example, the vaccinating nozzle 400 can be angled to face the piglet and is configured to spray in a fan action delivering the entire dose of vaccine in an appropriate diluent. This spray nozzle arrangement is advantageous due to the fact that piglets tend to face down when standing or moving from one spot to another spot.

The spray nozzle 400 can be located along the floor of the housing 110 or it can be located along the bottom sections of one or more of the walls 130, 140 so long as the nozzle sprays upwardly toward the face of the piglet. The spray nozzle 400 can be recessed within a slot or compartment in the floor 120 and a screen or the like can be provided over the recess to prevent the piglet from stepping on the spray nozzle 400.

In one embodiment, the spray nozzle 400 is of a type that has a variable spray feature in that the spray characteristics of the nozzle 400 can be varied depending upon the particular application. For example, the nozzle 400 includes a nozzle head 410 that can be manipulated (e.g., rotated) to change the spray characteristics or spray pattern. In one setting, the spray nozzle 400 can be configured to deliver a fine mist; in another embodiment, it delivers a course mist; in another embodiment, it delivers a pulsed spray, etc.

In another embodiment, the spray nozzle 400 is of a movable type in that once activated, the spray nozzle 400 can rotate or pivot so as to deliver the vaccine over a target area as opposed to spraying a straight stream. The range of movement of the nozzle 400 is designed so as to spray toward and into the face of the piglet before the piglet exits the housing 110.

As shown in FIGS. 1 and 2, in the illustrated embodiment, the spray nozzle 400 that is associated with the floor 120 is positioned close to the exit 160 and beyond the sensor 300 such that the sensor 300 detects the piglet first and then as the piglet continues to move toward the exit 160, the piglet walks into the spray that is being discharged from the nozzle 400, thereby being exposed to the dose of vaccination.

Figure 3:
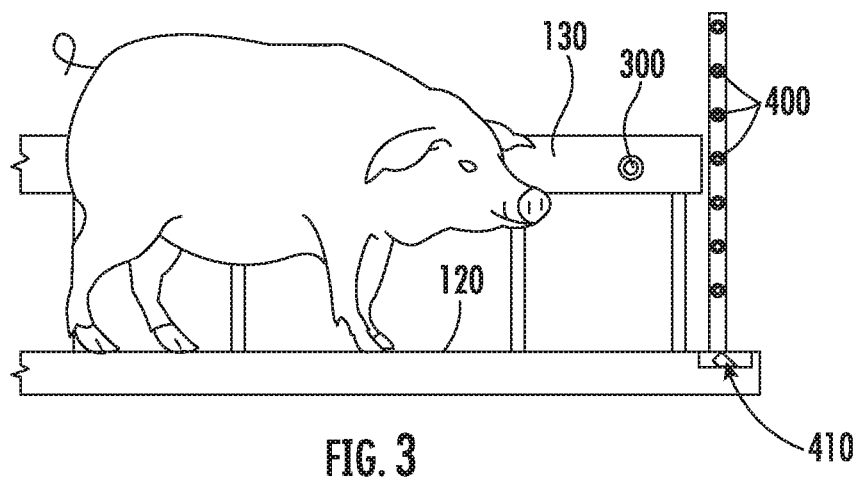
FIG. 3 is a side elevation view of a swine spray vaccination system according to another embodiment.
Figure 4:
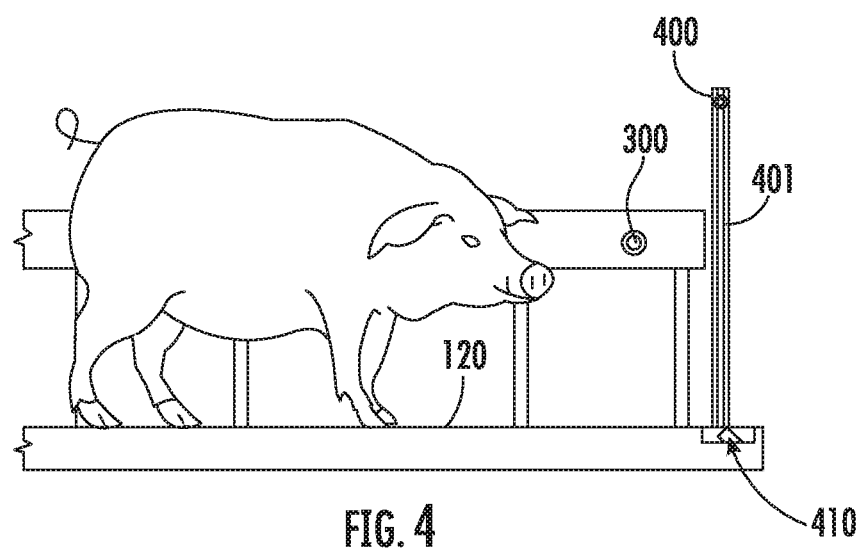
FIG. 4 is a side elevation view of a swine spray vaccination system according to yet another embodiment.

In yet another embodiment, shown in FIGS. 3 and 4, in addition to the vaccine spray coming from the bottom of the housing 110 (the floor), the vaccine can also be sprayed from sides aimed at the nose, eyes and mouth to immunize both the conjunctive associated lymphoid system (CALT) and the gut associated lymphoid system (GALT). The spray nozzles 400 are associated with one or more of the side walls 130, 140. In particular, the spray nozzles 400 are positioned along the side walls 130, 140 so as to direct the vaccine upwardly toward the facial area of the piglet.

FIG. 3 shows a plurality of spray nozzles 400 oriented vertically along one or both of the side walls 130, 140. Each of the spray nozzles 400 communicate with a controller and are fluidly connected to a source of vaccine such that the controller can instruct one or more of the nozzles 400 to be actuated to discharge the vaccine dose. Thus, when larger animals are being sprayed, the controller will select one or more spray nozzles 400 that are at an elevated height and conversely, when smaller animals are being sprayed, the controller can instruct one or more lower spray nozzles 400 to be actuated. The actuation of the spray nozzles 400 can be triggered based on input from the sensor 300. A plurality of optical beams disposed at varying heights can be triggered to determine the height of each piglet. Based on the height determined by the sensor 300, the particular spray nozzles 400 can be triggered for an optimal discharge pattern into the piglet's facial area. Further, a similar determination can be made using a weight sensor and a relationship between the mass of the piglet and height.

Each nozzle 400 is fluidly connected to the source using conventional means, such as a conduit, and each of the conduits from the nozzles 400 can be fluidly connected to a main line that leads to the source.

In yet another embodiment shown in FIG. 4, the spray nozzles 400 that are associated with at least the side walls 130, 140 are adjustable in nature to permit the spray nozzles to be positioned at a desired distance from the floor 120. For example, the spray nozzles 400 can be part of a track system in which the spray nozzle 400 is securely held within a vertical track member 401. Any number of different mechanisms, including clamps, etc., can be used to hold the spray nozzle 400 within the track at a predetermined location thereof and thus, at a predetermined distance from the floor 120.

The spray nozzles 400 can be automatically or manually adjusted. For example, the spray nozzles 400 can be part of a motorized assembly in which the location of the spray nozzles 400 can be changed by instructing a motor to drive the nozzles 400 along a vertical track 401 to a desired height. For example, when larger piglets are herded and directed into the housing 110, the nozzles 400 are moved to a higher height so that the vaccination spray therefrom is directed at the facial area of the piglet. In both the manual and automatic arrangements, the nozzle 400 travels along the track 401 (vertical track) to permit the nozzle 400 to be positioned at a select distance (height) from the floor 120 of the housing 110. The automated adjustment can also be made similar to the above embodiment using input from the sensor 300 to determine the height of the piglet.

It will be appreciated that even when nozzles 400 are included on the side walls 130, 140, the nozzles 400 are still oriented relative to the facial area of the piglet such that the vaccine is sprayed upwardly into the facial area of the piglet regardless of the size of the piglet.

Accordingly, in contrast to traditional spray mechanisms designed for chicks, the spray component (nozzles 400) of the system 100 works from the base up rather than the top down as for the chicks. Additionally, the time of vaccination is different for chicks who are normally vaccinated soon after hatch and in the present system 100, the piglets are vaccinated at the time of weaning. This time is also an opportune time for the vaccination as maternal antibodies are waning at 15-18 days of age when the vaccination is completed.

The timing of the spray vaccination is such that once the sensor 300 is triggered upon detection of a piglet in the vaccination station 200, the vaccine is immediately applied via a spray and the nozzles 400 are positioned so that even if the piglet continues to move toward the exit 160, there is sufficient time for the entire vaccine dose to be applied to the facial area of the piglet.

After receiving the vaccine dose, the piglet continues toward and exits the system 100 through the exit 160. At which time, another piglet enters the vaccination station 200 where it is sprayed with vaccine as described above.

Figure 6:
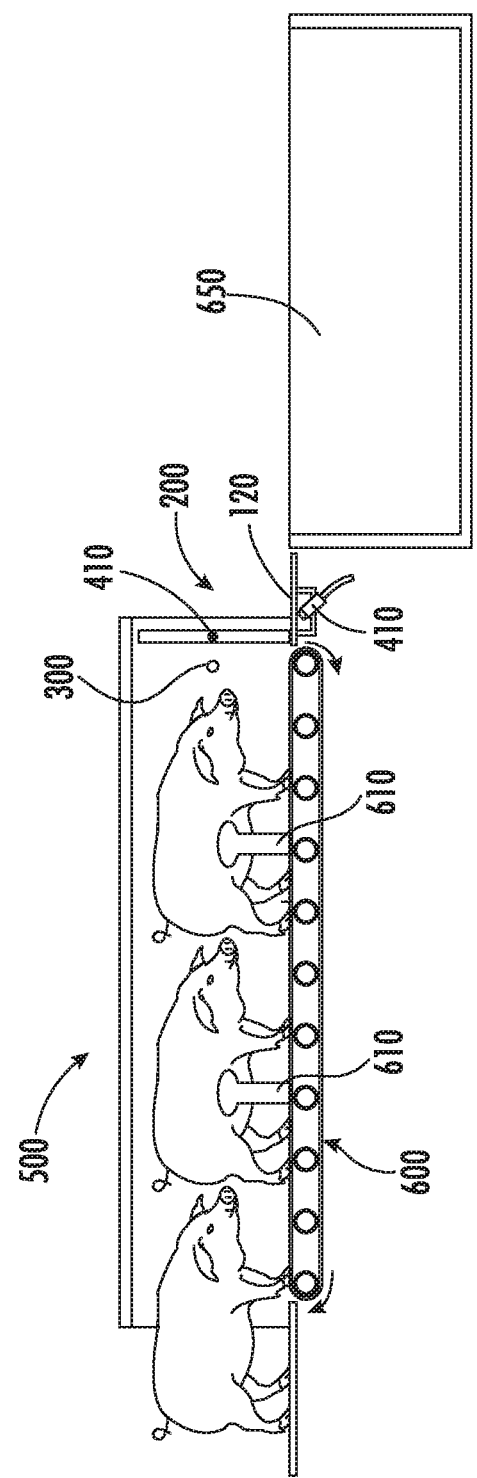
FIG. 6 is a side elevation, in partial cross-section, of a swine spray vaccination system according to another embodiment.

Now turning to FIG. 6 in which another vaccination system 500 according to another embodiment is illustrated. The system 500 is similar to the system 100 and includes a number of elements common in the system 100; however, the system 500 is configured to include a means 600 for transporting the piglet into and/or through the system 500. The means 600 is an automated means that is constructed to move the piglet from one location to another location and in particular, from a location outside of the housing 110 to the vaccination station 200 and then to a location outside of the housing 110 post vaccination.

In one embodiment, the means 600 is in the form of a conveyor, such as an endless loop conveyor, that is arranged to run at least partially along the floor 120 of the housing 110. This arrangement permits the piglets to be individually fed and loaded on the conveyor 600 and then delivered to the vaccination station 200 where they are individually vaccinated.

In addition, the means 600 (conveyor) includes a device or mechanism 610 for grasping or holding the piglet as it is moved along toward and into the vaccination station 200. The device 610 can be in the form of a post or clamp device that grasps and holds the piglet. The device 610 thus serves to restrain and limit the movement of the piglet as the means 600 transports the piglet from one location to the other location. Once the piglet is vaccinated, the device 610 is either manually or automatically disengaged to release the piglet. In any event, the piglet is released from the device 610 and is free to be moved to another location post vaccination.

The system 500 can also include a receptacle 650 that that receives the piglets post vaccination. In the illustrated embodiment, the receptacle 650 is in the form of a crate or the like. In this embodiment, the conveyor 600 is configured so that the piglets are directed into the receptacle 650 after each piglet has been individually vaccinated.

In the embodiment of FIG. 6, the main spray nozzle 400 can be still associated with the floor 120 in that it the conveyor 600 does not have to occupy the complete width of the floor 120 but can be a section thereof. Thus, the spray nozzle 400 can be formed to one side of the conveyor 600 but is still configured so that is sprays upwardly so as to deliver the vaccine dose to the facial area of the piglet. Alternatively, as shown, the floor 120 can be located adjacent one end of the conveyor 600 such that the piglets are delivered to the floor 120 or over the floor 120 to be placed into position where they are vaccinated.

Figure 7:
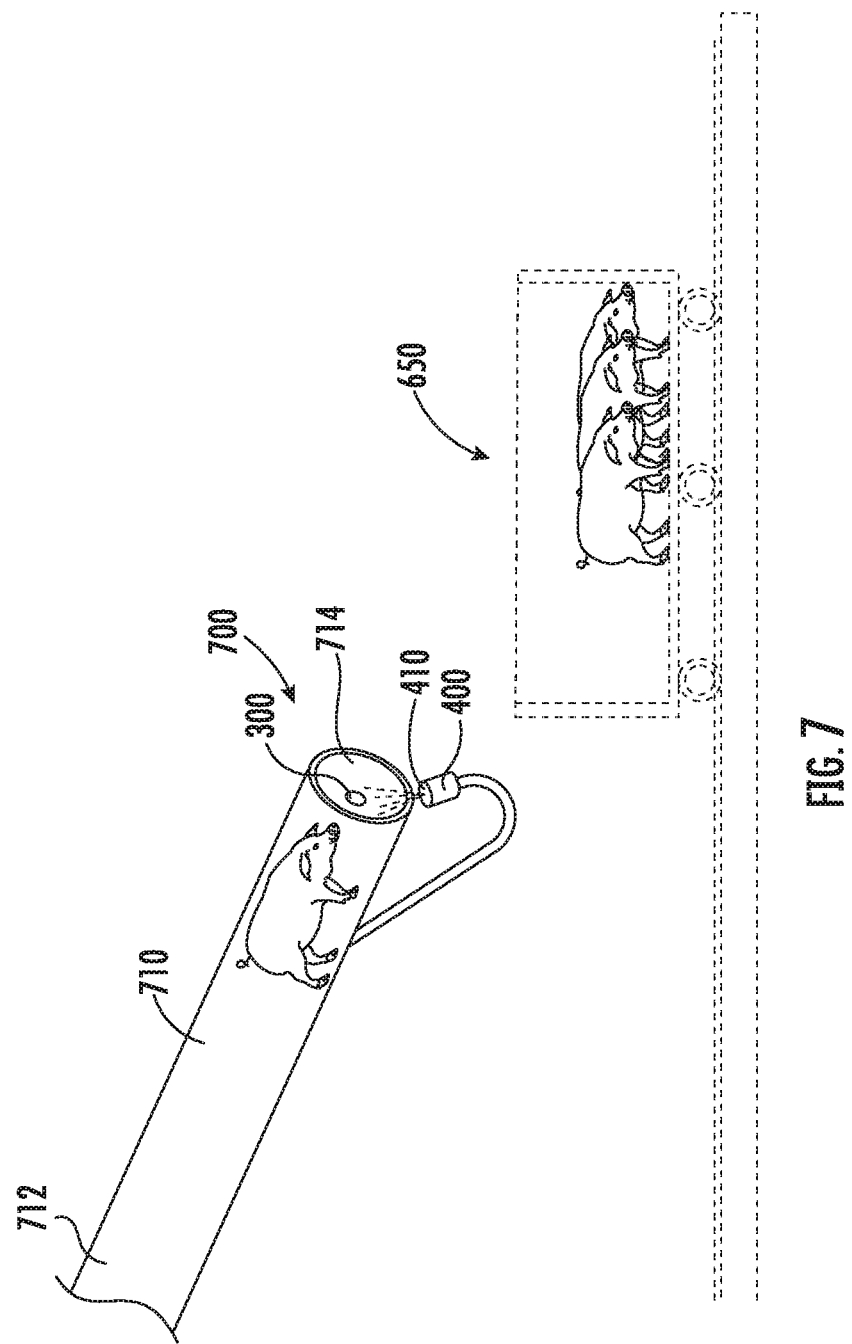
FIG. 7 is a side perspective view, in partial cross-section, of a swine spray vaccination system according to another embodiment.

In traditional handling arrangements, piglets are handled by personnel and moved to a receptacle, like crate 650, as the personnel wean them from the sow. The practice is to hold the piglets by their hind legs and then drop the piglets into the receptacle 650 that is then used to move them to a grow out area. In the embodiment illustrated in FIG. 7, a vaccination system 700 is provided that is designed for use with receptacle 650. The vaccination system 700 is configured in the form of a chute 710 that includes a first end or entrance 712 and an opposite second end or exit 714 that is positioned proximate the receptacle 650 such that when the piglet exits the chute 710, it is delivered into the receptacle 650. For example, the exit 714 can be operably attached to the receptacle 650 to permit the piglet to be delivered into the receptacle 650.

The chute 710 is constructed similar to the housing 110 of FIG. 1 in that it includes one or more sensors 300 and one or more spray nozzles 400 for delivering a vaccine dose to the facial area of the piglet as it travels within the chute 710. For example, the chute 710 has incorporated therein one or more sensors 300 to detect the presence of the piglet at a target area. Since the chute 710 is inclined at an angle that causes the inserted piglet to slide down the chute 710 toward the exit 714, the sensor 300 is located and is configured to detect the piglet as it slides within the chute 710. In one embodiment, the sensor 300 is in the form of an optical sensor and it detects the piglet as soon as the piglet breaks the beam emitted by the optical sensor 300. As with the other system, the triggering of the sensor 300 causes a control signal to be sent to the master controller which then communicates with and instructs the spray nozzle 400 to administer the vaccine dose.

Accordingly, downstream of the sensor 300 one or more spray nozzles 400 are provided inside the chute 710. As with all other embodiments, the spray nozzles 400 are positioned so as to spray the vaccine dose in an upwardly manner so that the vaccine dose is delivered to the facial area of the piglet. Since the chute 710 can be a cylindrical tube structure, at least one spray nozzle 400 is disposed along the floor or bottom of the chute 710 to ensure that the vaccine dose is administered to the facial area (snout) of the piglet. The spray nozzle(s) 400 can thus be located close to the exit 714 of the chute 710 or they can be located closer to the middle or the chute 710. While the chute 710 preferably includes one spray nozzle 400 along the floor of the chute 710, it also can include one or more nozzles 400 that are located at higher (elevated) positions relative to the nozzle 400 that is formed along the floor of the chute 710.

As with the other embodiments, the sensor 300 is not limited to being a motion (optical) sensor but it can be other sensors including a mass (weight) sensor.

The exit 714 of the chute 710 can be positioned so that receptacle 650 can move thereunder. Thus, once one receptacle 650 is filled, it can be moved and another can be delivered underneath the chute 710 without moving the chute 710.

Figure 8:
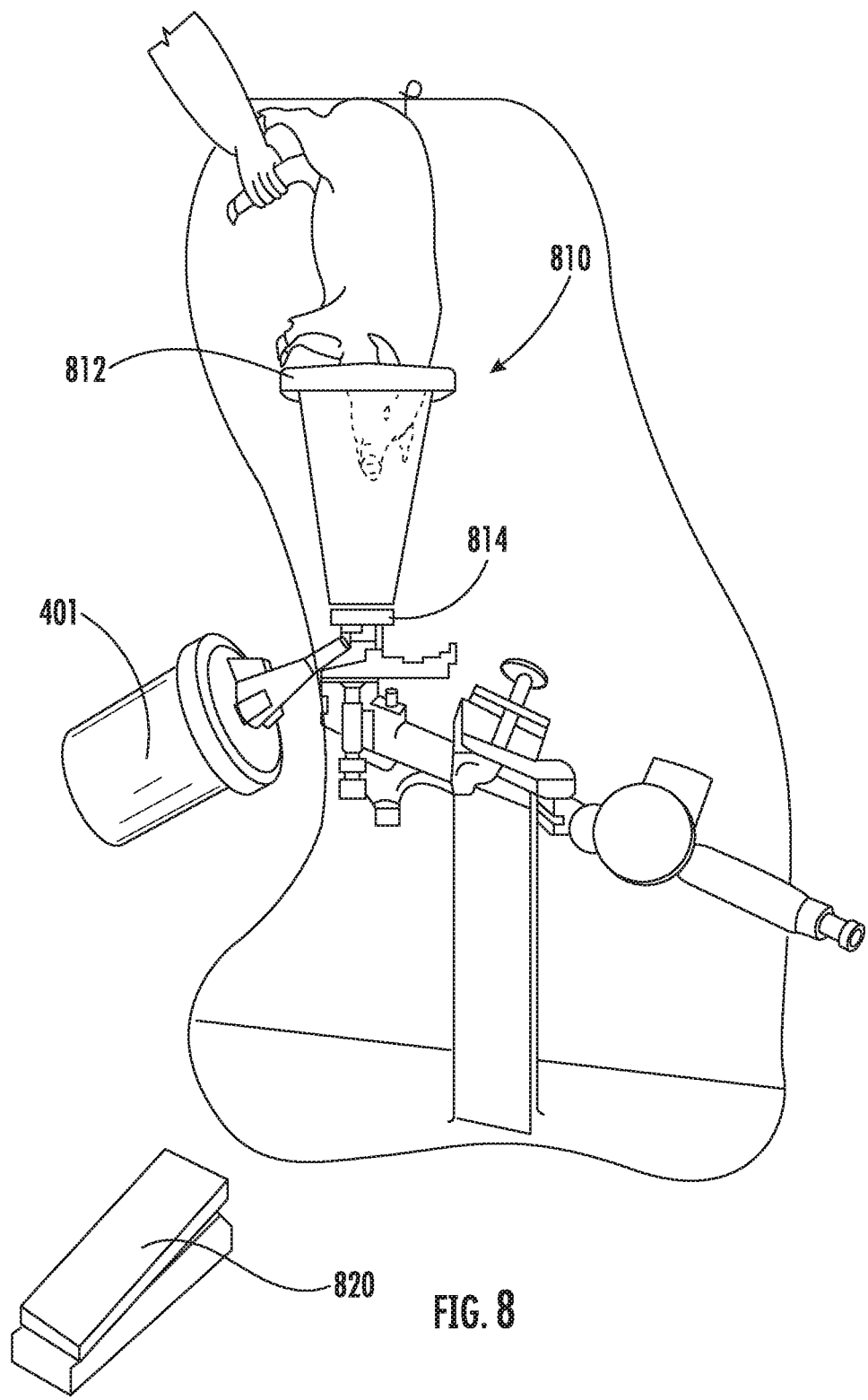
FIG. 8 is a perspective of a swine spray vaccination system according to yet another embodiment.

In yet another embodiment shown in FIG. 8, a spray vaccination system 800 is illustrated and includes a spray applicator 810 in the form of a cone that has at least one open end 812 that represents the greatest diameter of the cone. The end 812 has a diameter that is great enough to permit at least the facial area (snout) of the piglet to be received therein. At an opposite end 814, the cone includes at least one spray nozzle (not shown) that is oriented to spray the vaccine dose toward the facial area of the piglet. As the piglets are moved, each piglet is held by its hind legs and is "dunked" into the cone 810 and the detection or presence of the snout activates the spray nozzle. The piglet can thus be grasped by its hind legs using an automated mechanism or the piglet can be held by its hind legs by a person who then maneuvers the upside down piglet to the spray vaccination system 800. Preferably, the piglet's head/snout fits tightly and neatly in the cone, thereby trapping the snout in the cone and preventing movement and allowing an accurate "take" of the vaccine.

The spray nozzle can be triggered to operate using any number of different techniques, including both manual and automated techniques. For example, when a manual technique is used, a lever, switch, button, etc., 820 is used to actuate the spray nozzle once the facial area of the piglet is in the proper position within the cone. In FIG. 8, the mechanism 820 is a foot activated actuator (e.g., foot pedal), whereupon, when the operator steps thereon, the spray mechanism is actuated for a prescribed period of time to discharge a dose of vaccination.

Alternatively, the spray nozzle is automatically actuated once the facial area of the piglet is detected. For example, one or more sensors (not shown) 819 can be employed with the cone and are configured to detect the facial area (snout) of the piglet (e.g., the snout of the piglet can break a beam that is part of an optical sensor). In another embodiment, the sensor is a touch activated sensor, whereby contact of the snout to the sensor sends a control signal to the master controller to cause a spray of the vaccine (the vaccine dose) to be generated and delivered to the facial area of the piglet. In all embodiments, the amount and time period that the spray is discharged can be controlled using any number of different techniques. For example, the spray nozzle can be deactivated as soon as the sensor no longer detects the piglet within the cone (e.g., when the beam of the optical sensor is restored). Alternatively, the spray nozzle is simply activated for a given amount of time that results in the desired quantity of vaccine being discharged from the spray nozzle. It will be understood that the spray volume can be adjusted to deliver the appropriate dose and droplet size of the vaccine can be adjusted for the best "lake" of the vaccine.

When automated, a number of piglets are successively "dunked" in the spray applicator 810.

In the illustrated embodiment, the spray nozzle includes a source 401 of vaccination and in particular, the source 401 can be in the form of a container or bottle that stores the vaccination. The source 401 is connected to the other operative components of the spray nozzle and therefore, once activated, the vaccination is withdrawn from the source 401 as by using a pump or the like and then discharged through the spray nozzle into the conically-shaped body 810. In order to permit "dunking" of the piglet, the cone shaped spray nozzle is vertically oriented with its opening facing upward. This allows the piglet to be easily held and inserted snout first into the spray nozzle.

The mechanism 800 can include other operative parts, including pressure regulators and indicators to show the level of the fluid in the source container 401, as well as whether the fluid in source container 401 is empty.

Figure 9:
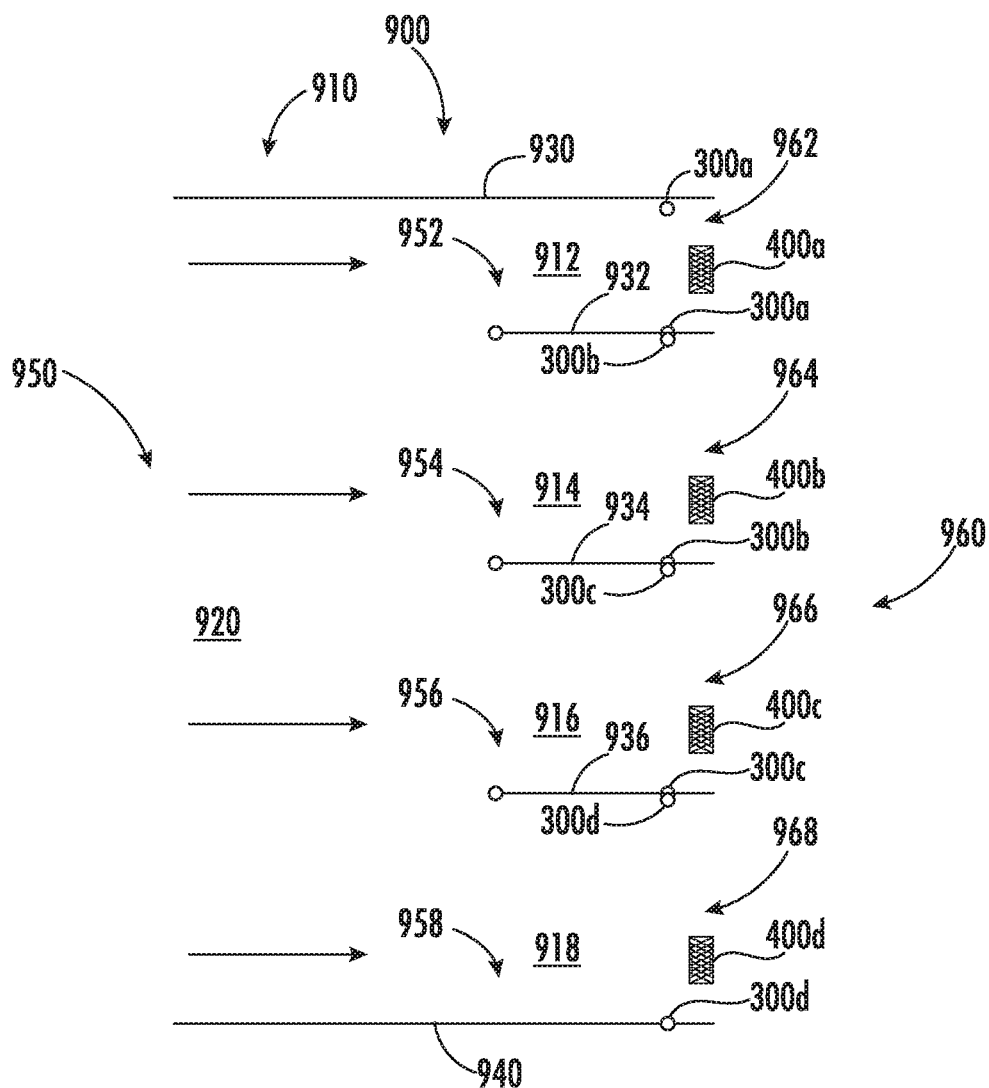
FIG. 9 is a top view of a swine spray vaccination system according to a further embodiment.

In a further embodiment, FIG. 9 illustrates system 900 utilizing a divided housing 910 that subdivides into smaller housings 912, 914, 916, 918. The housing 910 further has a floor 920 and first and second side walls 930, 940 disposed perpendicular to the floor 920. Intermediate walls 932, 934, 936 are disposed within the housing between the first and second side walls 930, 940 and can be equally spaced apart. The intermediate walls 932, 934, 936 can form each of the smaller housings 912, 914, 916, 918 which are sized to accept one piglet. In the illustrated embodiment, first and second side walls 930, 940 and the intermediate walls 932, 934, 936 are disposed parallel to each other, in chute fashion. However, all or some of the walls 930, 932, 934, 936, 940 can be non-parallel to each other to form "V" shapes for the housing 110 or smaller housings 912, 914, 916, 918.

In operation, a number of piglets enter the housing via an entrance 950 located on one end of the housing. As the piglets move through the housing 110 they encounter the intermediate walls 932, 934, 936, which lead to sub-entrances 952, 954, 956, 958 dividing individual piglets into each of the smaller housings 912, 914, 916, 918. As the piglet enters the smaller housings 912, 914, 916, 918 it triggers sensor 300 which in turn activates spray nozzle 400 to discharge in the facial area of each piglet. In a particular embodiment, each spray nozzle 400a, 400b, 400c, 400d is disposed at or near the exit of the housing 960 which is divided in sub-exits 962, 964, 966, 968 for each of the smaller housings 912, 914, 916, 918. Further, each spray nozzle can be controlled by an individual sensor 300a, 300b, 300c, 300d or can be generally trigged by sensor 300 as piglets move through the sub-entrances 952, 954, 956, 958. As noted above, spray nozzles 400 can be fixed, or movable, but positioned to discharge generally upwards and into the facial area of the piglet.

The age of the swine will depend upon which vaccination is being applied. For example, the swine can have an age of 15 to 18 days which is a suitable age for applying a number of different vaccinations. Vaccinations that can be delivered by the above can include, but are not limited to vaccinations for Atrophic rhinitis (*Pasteurella multocida* type A and toxigenic type D, *Bordetella bronchiseptica*, *E. Coli*, Erysipelas (*Erysipelothrix rhusiopathiae*), Leptospirosis, Traditional and New Swine Flues, the Porcine Circovirus (PCV), the PRRS virus, and *Mycoplasma hyopneumoniae*.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. Doubtless numerous other embodiments can be conceived that would not depart from the teaching of the present invention whose scope is defined by the following claims.

That which is claimed:

1. A method for vaccinating swine, comprising the steps of:
   directing a plurality of piglets each having a facial area into a first end of a housing;
   metering the plurality of piglets to form a single file line of individual piglets directed into the housing toward a vaccination station associated therewith, the vaccination station having one or more spray nozzles mounted therein;
   sensing each individual piglet entering the vaccination station;
   selecting at least one of the one or more spray nozzles arranged to be upwardly inclined relative to the facial area of the individual piglet wherein the one or more spray nozzles is positioned along a vertical track member of a track system associated with the vaccination station and is arranged to be upwardly inclined, the one or more spray nozzles being automatically adjusted according to a height of the facial area of each individual piglet, via movement of the one or more spray nozzles along the vertical track member by a motorized assembly, such that the at least one of the one or more spray nozzles is directed along the upward inclination toward the facial area of the individual piglet;
   actuating the selected at least one of the one or more spray nozzles to emit a spray of a vaccine along the upward inclination into engagement with the facial area of each of the individual piglets; and
   directing the individual piglet toward a second end of the housing to exit the housing.

2. The method of claim 1, wherein the selecting and actuating steps automatically occur once each individual piglet is sensed by the sensing step.

3. The method of claim 1, wherein the housing comprises a narrowing chute that directs the piglets toward the second end such that the piglets are metered into a single file line through the vaccination station by the narrowing chute, the narrowing chute having a pair of inwardly angled side walls.

4. The method of claim 3, wherein the narrowing chute is associated with the vaccination station and includes a plurality of narrowing chute spray nozzles positioned along the side walls, with the narrowing chute spray nozzles arranged to be upwardly inclined toward the facial area of the individual piglets.

5. The method of claim 1, wherein the at least one of the one or more spray nozzles is configured to be adjustable to change at least one of spray characteristics and a spray pattern of the spray of the vaccine.

6. The method of claim 1, wherein the at least one of the one or more spray nozzles is movable so as to rotate or pivot to emit the vaccine along the upward inclination into engagement with the facial area of the individual piglet.

7. The method of claim 1, wherein the vaccine is administered to immunize the conjunctive associated lymphoid system and the gut associated lymphoid system.

8. A method for vaccinating swine, comprising the steps of:

directing a plurality of piglets each having a facial area into a first end of a housing, the housing including a narrowing chute arranged to meter the piglets into a single file line of individual piglets and to direct the individual piglets through a vaccination station toward a second end of the housing, the vaccination station having one or more spray nozzles mounted therein and arranged in communication with and to be selectively actuated by a controller;

sensing a height of the facial area of each individual piglet, using one or more optical beam sensors, upon each individual piglet entering the vaccination station;

selecting at least one of the one or more spray nozzles arranged to be upwardly inclined toward the facial area of the individual piglet from the sensed height of the facial area;

actuating the selecting at least one of the one or more spray nozzles to emit a spray of a vaccine along the upward inclination into engagement with the facial area of each of the individual piglets; and directing the individual piglet toward a second end of the housing to exit the housing.

9. The method of claim 8, wherein the vaccine is administered to immunize the conjunctive associated lymphoid system and the gut associated lymphoid system.

* * * * *